(12) United States Patent
Bartels et al.

(10) Patent No.: US 10,829,500 B2
(45) Date of Patent: *Nov. 10, 2020

(54) PYRIDYL-TRIAZABICYCLES

(71) Applicant: Hoffmann-La Roche Inc., Little Falls, NJ (US)

(72) Inventors: Bjoern Bartels, Schopfheim (DE); Cosimo Dolente, Allschwil (CH); Wolfgang Guba, Muellheim (DE); Wolfgang Haap, Loerrach (DE); Andreas Kuglstatter, Loerrach (DE); Ulrike Obst Sander, Reinach BL (CH); Jens-Uwe Peters, Grenzach-Wyhlen (DE); Mark Rogers-Evans, Bottmingen (CH); Thomas Woltering, Freiburg (DE); Christian Schnider, Basel (CH); Roger Wermuth, Sissach (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,307

(22) Filed: Jul. 31, 2019

(65) Prior Publication Data

US 2019/0352312 A1 Nov. 21, 2019

Related U.S. Application Data

(63) Continuation of application No. 16/029,228, filed on Jul. 6, 2018, now Pat. No. 10,414,780, which is a continuation of application No. 15/314,718, filed as application No. PCT/EP2015/066600 on Jul. 21, 2015, now Pat. No. 10,047,102.

(30) Foreign Application Priority Data

Jul. 25, 2014 (EP) .................................. 14178503

(51) Int. Cl.
| | |
|---|---|
| C07D 513/04 | (2006.01) |
| A61K 31/549 | (2006.01) |
| C07D 417/04 | (2006.01) |
| A61P 25/28 | (2006.01) |

(52) U.S. Cl.
CPC .......... *C07D 513/04* (2013.01); *A61K 31/549* (2013.01); *A61P 25/28* (2018.01); *C07D 417/04* (2013.01)

(58) Field of Classification Search
CPC .................................................... C07D 513/04
USPC ............................................................ 514/211
See application file for complete search history.

(56) References Cited

U.S. PATENT DOCUMENTS 10,047,102 B2 * 8/2018 Bartels ................. A61P 25/28
10,414,780 B2 * 9/2019 Bartels ................. A61K 31/549

* cited by examiner

Primary Examiner — Kahsay Habte

(57) ABSTRACT

The present invention provides a compound of formula I

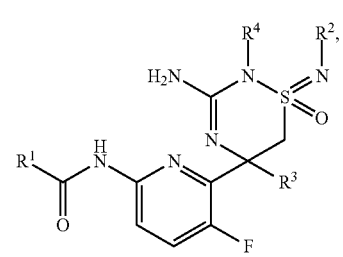

having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

12 Claims, No Drawings

PYRIDYL-TRIAZABICYCLES

CROSS-REFERENCE TO RELATED APPLICATIONS

This application is a Continuation of U.S. patent application Ser. No. 16/029,228, filed Jul. 6, 2018, which in turn is a Continuation Application of U.S. patent application Ser. No. 15/314,718, filed Nov. 29, 2016, now U.S. Pat. No. 10,047,102, which in turns claims benefit from 371 National Stage Application of PCT/EP2015/066600, filed Jul. 21, 2015, which claims priority from European Patent Application No. 14178503.0, filed on Jul. 25, 2014, which are all hereby incorporated by reference in all of their entireties.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36):26326). It is thus presumed that inhibitors of BACE1 activity can be useful agents for therapeutic intervention in Alzheimer's disease (AD).

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides triazabicycles having BACE1 inhibitory properties, their manufacture, pharmaceutical compositions containing them and their use as therapeutically active substances.

SUMMARY OF THE INVENTION

The present invention provides a compound of formula I,

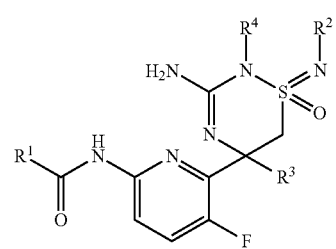

wherein the substituents and variables are as described below and in the claims, or a pharmaceutically acceptable salt thereof.

The present compounds have Asp2 β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methylpropyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl (pyrimidyl), pyrrolyl, quinolinyl, tetrazolyl, thiazolyl, thienyl, triazolyl, 6,7-dihydro-5H-[1]pyrindinyl and the like. A particular "heteroaryl" is pyridinyl. A specific "heteroaryl" is pyridin-2-yl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

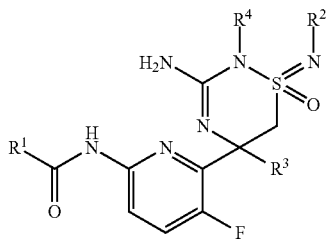

I wherein
$R^1$ is selected from the group consisting of
  i) aryl,
  ii) aryl, substituted by 1-3 substituents individually selected from cyano, $C_{1-6}$-alkyl, halogen-$C_{1-6}$-alkyl and halogen
  iii) heteroaryl,
  iv) heteroaryl, substituted by 1-3 substituents individually selected from cyano, $C_{1-6}$-alkyl, halogen-$C_{1-6}$-alkyl and halogen, and $R^2$ together with $R^4$ is selected from the group consisting of
  i) —$(CH_2)_x$—, wherein x=3 or 4; substituted by 1 or 2 halogen-$C_{1-6}$-alkyl, and
  ii) —$(CH_2)$—$(CY_2)_z$—$(CH_2)$—, wherein each individual Y=H or F and z=1 or 2;

$R^3$ is selected from the group consisting of
  i) $C_{1-6}$-alkyl, and
  ii) halogen-$C_{1-6}$-alkyl;
or pharmaceutically acceptable salts thereof.

A certain embodiment of this invention relates to a compound of formula I as described herein, wherein
$R^1$ is selected from the group consisting of
  i) aryl,
  ii) aryl, substituted by 1-3 substituents individually selected from cyano, $C_{1-6}$-alkyl, halogen-$C_{1-6}$-alkyl and halogen
  iii) heteroaryl,
  iv) heteroaryl, substituted by 1-3 substituents individually selected from cyano, $C_{1-6}$-alkyl, halogen-$C_{1-6}$-alkyl and halogen, and $R^2$ together with $R^4$ is —$(CH_2)_x$—, wherein x=3 or 4;
$R^3$ is selected from the group consisting of
  i) $C_{1-6}$-alkyl, and
  ii) halogen-$C_{1-6}$-alkyl;
or pharmaceutically acceptable salts thereof.

A certain embodiment of this invention relates to a compound of formula I as described herein, which is of formula Ia, wherein $R^1$, $R^2$, $R^4$ and $R^4$ are as described herein.

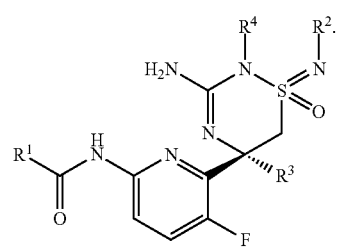

Ia

A certain embodiment of this invention relates to a compound of formula I as described herein, which is of formula Ic, wherein $R^1$, $R^2$, $R^4$ and $R^4$ are as described herein.

Ic

A certain embodiment of this invention relates to a compound of formula I as described herein, which is of formula Id, wherein $R^1$, $R^2$, $R^4$ and $R^4$ are as described herein.

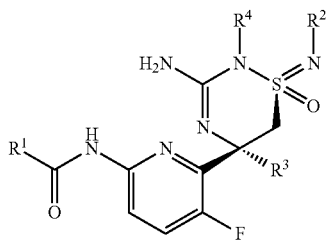

A certain embodiment of this invention relates to a compound of formula I as described herein, wherein $R^1$ is heteroaryl, substituted by 1-2 substituents individually selected from cyano and $C_{1-6}$-alkyl.

A certain embodiment of this invention relates to a compound of formula I as described herein, wherein $R^1$ is pyridyl, substituted by 1-2 substituents individually selected from cyano and $C_{1-6}$-alkyl.

A certain embodiment of this invention relates to a compound of formula I as described herein, wherein $R^1$ is 5-cyano-3-methyl-pyridin-2yl or 5-cyano-pyridin-2yl.

A certain embodiment of this invention relates to a compound of formula I as described herein, wherein $R^2$ and $R^4$ together are —(CH$_2$)—(CY$_2$)$_z$—(CH$_2$)—, Y is H and z is 2.

A certain embodiment of this invention relates to a compound of formula I as described herein, wherein $R^3$ is methyl.

A certain embodiment of this invention relates to a compound of formula I as described herein, wherein $R^3$ is —CH$_2$F.

A certain embodiment of this invention relates to a compound of formula I as described herein that is selected from the group consisting of
5-Cyano-pyridine-2-carboxylic acid [6-((3R,4aR)-1-amino-3-methyl-4a-oxo-3,4,6,7,8,9-hexahydro-4a$\lambda^6$-thia-2,5,9a-triaza-benzocyclohepten-3-yl)-5-fluoro-pyridin-2-yl]-amid,
5-Cyano-pyridine-2-carboxylic acid [6-((3R,4aS)-1-amino-3-methyl-4a-oxo-3,4,6,7,8,9-hexahydro-4a$\lambda^6$-thia-2,5,9a-triaza-benzocyclohepten-3-yl)-5-fluoro-pyridin-2-yl]-amide,
5-Cyano-3-methyl-pyridine-2-carboxylic acid [6-((3R,4aS)-1-amino-3-methyl-4a-oxo-3,4,6,7,8,9-hexahydro-4a$\lambda^6$-thia-2,5,9a-triaza-benzocyclohepten-3-yl)-5-fluoro-pyridin-2-yl]-amide,
N-[6-[(1S,10S)-8-Amino-10-(fluoromethyl)-1-oxo-1$\lambda^6$-thia-2,7,9-triazabicyclo[5.4.0]undeca-1,8-dien-10-yl]-5-fluoropyridin-2-yl]-5-cyanopyridine-2-carboxamide, and
N-[6-[(1R,10S)-8-Amino-10-(fluoromethyl)-1-oxo-1$\lambda^6$-thia-2,7,9-triazabicyclo[5.4.0]undeca-1,8-dien-10-yl]-5-fluoropyridin-2-yl]-5-cyanopyridine-2-carboxamide.

A certain embodiment of the invention relates to a process comprises reacting a compound of formula XI' with a compound of formula XII' to a compound of formula I.

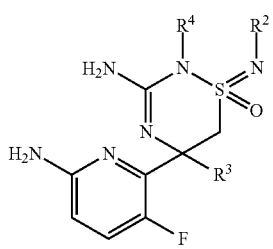

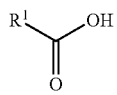

wherein $R^1$, $R^2$, $R^3$ and $R^4$ are as defined herein.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

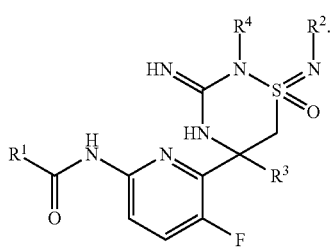

Ie

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

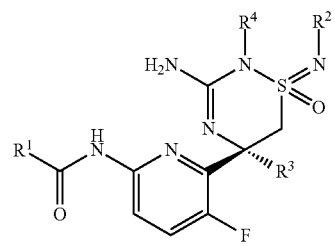

Ia

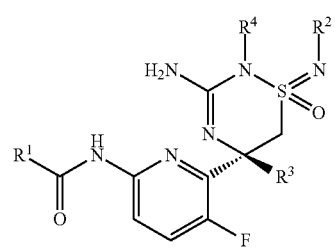

Ib

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I can be prepared through a number of synthetic routes for example as illustrated in scheme 1. The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the scheme 1 can be isolated and purified by methods known to those skilled in the art, such as but not limited to ion exchange chromatography, solid phase extraction, liquid-liquid extraction, silica chromatography, crystallization and preparative HPLC.

In more detail, compounds of formula I according to the present invention can be prepared by the methods and procedures given below. Some typical procedures for the preparation of compounds of formula I are illustrated in scheme 1.
Scheme 1: Synthesis of compounds I
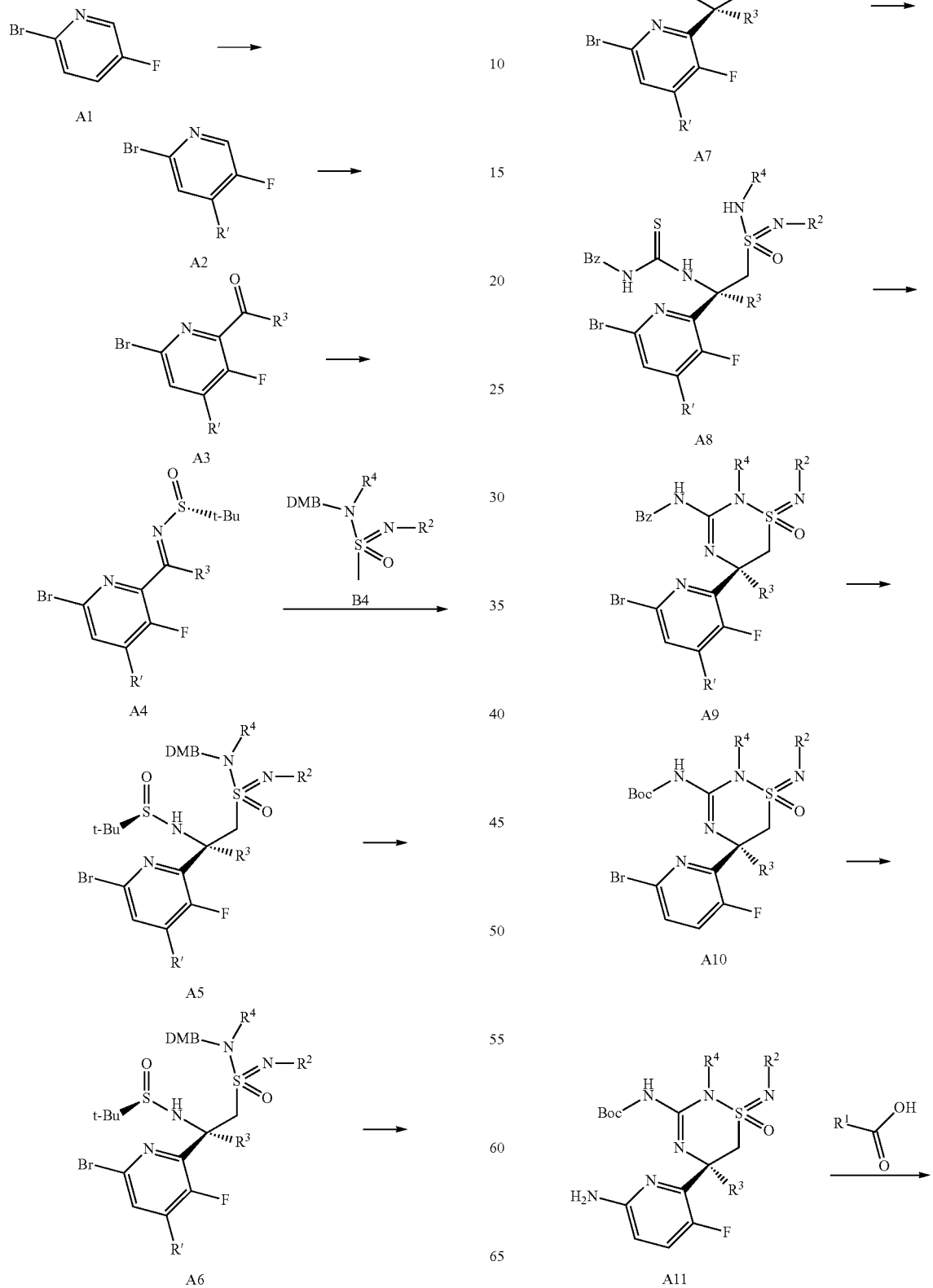

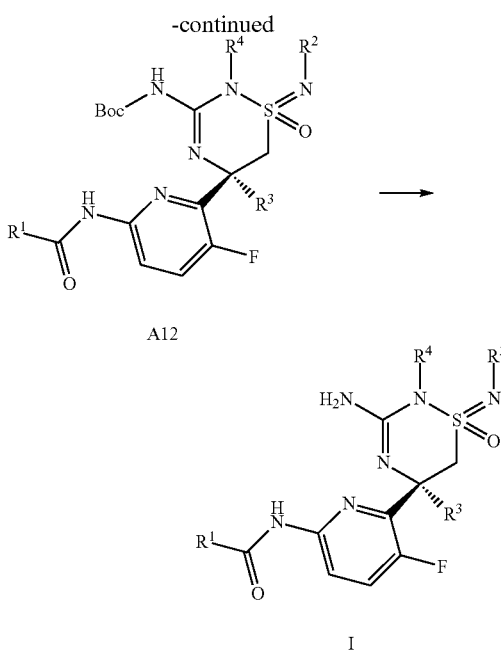

A12

I

Non-commercial aryl ketones of general formula A3 can be synthesized from the silyl protected pyridine A2 prepared from pyridine A1 by reaction with a strong base, e.g. LDA and an alkylchlorosilane, preferably triethylchlorosilane in an inert aprotic solvents such as tetrahydrofuran or diethyl ether. The protected pyridine A2 can then be reacted again with a strong base, e.g. LDA and an amide, e.g. an acetamide for $R^3$=Me, preferably N,N-dimethylacetamide, or LDA and an ester, e.g. ethyl difluoroacetate for $R^3$=CHF$_2$ or methyl fluoroacetate for $R^3$=CH$_2$F, in an inert aprotic solvents such as tetrahydrofuran or diethyl ether to give the desired aryl ketone A3.

Sulfinyl imines of formula A4 can be prepared in analogy to T. P. Tang & J. A. Ellman, J. Org. Chem. 1999, 64, 12, by condensation of an aryl ketone of formula B3 and a sulfinamide, e.g. an alkyl sulfinamide, most particularly (R)-tert-butylsulfinamide or (S)-tert-butylsulfinamide, in the presence of a Lewis acid such as e.g. a titanium(IV)alkoxide, more particularly titanium(IV)ethoxide, in a solvent such as an ether, e.g. diethyl ether or more particularly tetrahydrofuran.

The conversion of sulfinyl imines of formula A4 to sulfonamides-sulfonimidamides of formula A5 can proceed stereoselectively by the chiral directing group as described by Tang & Ellman. The sulfinyl imines of formula A4 can be reacted in an addition reaction with a lithiated sulfonimidamide, generated from a sulfonimidamide of formula B4 and a base such as n-butyllithium, lithium hexamethyldisilazid or LDA, in a solvent such as an ether, e.g. diethyl ether or more particularly tetrahydrofuran, at low temperatures, preferably −78° C.

The conversion of the sulfonamides-sulfonimidamides of formula A5 where R'=SiEt$_3$ to the desilylated sulfonamides-sulfonimidamides of formula A6 where R'=H can be effected with tetrabutylammonium fluoride or preferably potassium fluoride in the presence of an acid e.g. acetic acid in an ether or an amide preferably in a mixture of THF and dimethylformamide at ambient to elevated temperature, particularly at 23 to 40° C.

Hydrolysis of the chiral directing group and the 2,4-dimethoxybenzyl group (DMB) of sulfonamides-sulfonimidamides of formula A6 where R'=H to give the aminosulfonimidamides of formula A7 can be accomplished by first treatment with a mineral acid, e.g. sulfuric acid or particularly hydrochloric acid, in a solvent such as an ether, e.g. diethyl ether, tetrahydrofuran or more particularly 1,4-dioxane, and second by treatment with a strong organic acid, e.g. trifluoroacetic acid, where both steps are preferably conducted at ambient temperature.

Reaction of the amino sulfonimidamides of formula A7 with an isothiocyanate such as benzoylisothiocyanate in solvents such as ethyl acetate, tetrahydrofuran or acetonitrile at temperatures between 0° C. and 80° C., preferably 23° C., affords the thiourea sulfonimidamides of formula A8.

The thiourea sulfonimidamides of formula A8 can be cyclized to the N-benzoylated amidine sulfonimidamides of formula A9 by dehydration through reaction with a carbodiimide, like e.g. dicyclohexylcarbodiimide, diisopropylcarbodiimide or N-(3-dimethylaminopropyl)-N'-ethylcarbodiimide hydrochloride (EDC.HCl), preferably EDC.HCl, in solvents such as ethyl acetate, tetrahydrofuran or acetonitrile, preferably acetonitrile, at temperatures between 23° C. and 100° C., preferably 80° C.

The switch of protecting groups from the N-benzoylated amidine sulfonimidamides of formula A9 to the N-tert-butoxycarbonylated amidine sulfonimidamides of formula A10 can be achieved in a two step procedure by first reaction with di-tert-butyldicarbonate (Boc$_2$O) in the presence of an amine base such as triethylamine or N-ethyl-N,N-diisopropylamine, in a solvent such as dichlormethane, tetrahydrofuran or acetonitrile, at temperatures between 0° C. and 40° C., preferably 23° C., to give the doubly acylated amidine sulfonimidamides of formula A18, and second selective removal of the benzoyl group by reaction of the doubly acylated amidine sulfonimidamides with an amine nucleophile, like e.g. diethylamine, dimethylamine or ammonia, preferably ammonia, in a solvent such as dichloromethane or tetrahydrofuran, preferably tetrahydrofuran, at temperatures between 0° C. and 40° C., preferably 23° C.

The conversion of the bromo group in formula A10 to the amine group in formula A11 can be performed by reaction with an azide, in particular sodium azide and a cooper (I) halide in particular copper (I) iodide in the presence of L-ascorbate and an alkyl-1,2-diamine in particular trans-N,N'-dimethylcyclohexane-1,2-diamine in a protic solvent such as an alcohol in particular ethanol and water at elevated temperature preferably approximately 70° C.

The coupling of the aromatic amine A11 with carboxylic acids ($R^1$—CO$_2$H) to give amides of formula A12 can be effected with T3P in an aprotic solvent such as EtOAc at ambient temperature; or alternatively the carboxylic acids ($R^1$—CO$_2$H) can be activated by using reagents such as oxalyl chloride or 1-chloro-N,N,2-trimethyl-1-propenylamine (Ghosez's reagent, CAS-no. 26189-59-3) in a chlorinated solvent such as dichloromethane at 0° C. followed by reaction with the aromatic amine A11 in the presence of an amine base such as triethylamine or diisopropylethylamine at 0° C. to ambient temperature.

The cleavage of the protecting tert-butoxy carbonyl groups in compounds of formula A12 to produce compounds of general formula I can be effected by acid, such as trifluoroacetic acid, in inert solvents, such as dichloromethane, at temperatures between 0° C. and ambient temperature.

Scheme 2: Synthesis of intermediates B4

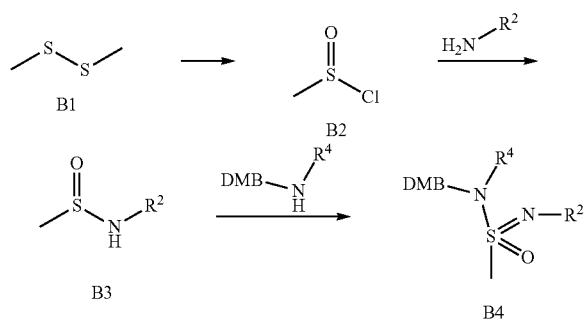

The methanesulfinyl chloride of formula B2 can be prepared by treatment of commercially available dimethyldisulfide of formula B1 with sulfuryl chloride and acetic acid at temperatures between −30° C. and 35° C. as described by Youn, Joo-Hack; Herrmann, Rudolf in *Tetrahedron Letters* 1986, 27(13), 1493-1494. The crude methanesulfinyl chloride of formula B2 can be purified by distillation or used directly in the next step to produce the sulfinamides of formula B3 which is achieved by simple reaction with an excess of an amine $R^2$—$NH_2$ or mixtures of an amine $R^2$—$NH_2$ with an amine base, such as triethylamine or N-ethyl-N,N-diisopropylamine, in a solvent such as dichlormethane or tetrahydrofuran, at temperatures starting as low as −78° C. and warming up to 0° C. or 23° C.

The sulfonimidamides of formula B4 can be prepared from the sulfinamides of formula B3 by reaction with a chlorinating reagent such as N-chlorosuccinamide or tert-butyl hypochlorite, preferably tert-butyl hypochlorite, in an inert solvent such as acetonitrile, tetrahydrofuran or dichloromethane, preferably dichloromethane, at temperatures starting as low as −78° C. and warming up to 0° C., to produce the intermediate sulfonimidoyl chlorides followed by reaction with an excess of an amine $R^4$—NHDMB or mixtures of an amine $R^4$—NHDMB with an amine base, such as triethylamine or N-ethyl-N,N-diisopropylamine at temperatures starting as low as −78° C. and warming up to 0° C. or 23° C. The amines $R^4$—NHDMB are generally prepared by a reductive amination of an amine $R^4$—$NH_2$ with 2,4-dimethoxybenzaldehyde by methods known to someone skilled in the art.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat # AL275C).

In a Perkin-Elmer White Optiplate-384 (Cat #6007290), 2 ul culture supernatants were combined with 2 μl of a 10× AlphaLISA Anti-hAβAcceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of A β 40 in the culture supernatants were calculated as percentage of maximum signal (cells treated with 1% DMSO without inhibitor). The $IC_{50}$ values were calculated using the Excel XLfit software.

TABLE 1

$IC_{50}$ values

| Exam. | Structure | BACE1 $IC_{50}$ [μM] |
|---|---|---|
| 1 | 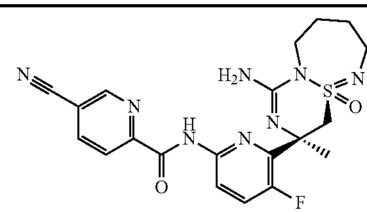 | 0.086 |
| 2 | 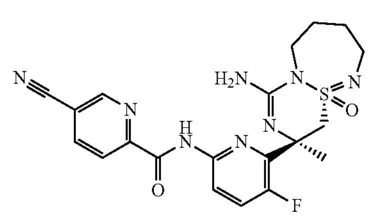 [SMILES: C[C@@]1(c2nc(NC(=O)c3ccc(C#N)cn3)ccc2F)C[S@@]2(=O)=NCCCCN2C(N)=N1] | 0.049 |

TABLE 1-continued

IC$_{50}$ values

| Exam. | Structure | BACE1 IC$_{50}$ [μM] |
|---|---|---|
| 3 | 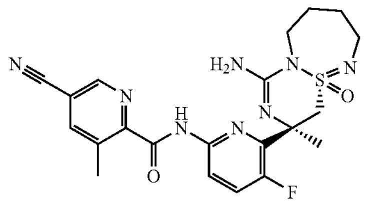 [SMILES: Cc1cc(C#N)cnc1C(=O)Nc1ccc(F)c([C@]2(C)C[S@@]3(=O)=NCCCCN3C(N)=N2)n1] | 0.036 |
| 4 | 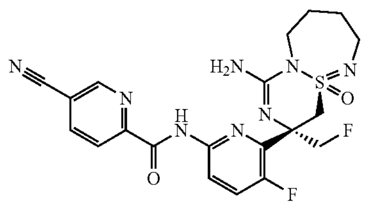 [SMILES: N#Cc1ccc(C(=O)Nc2ccc(F)c([C@]3(CF)C[S@]4(=O)=NCCCCN4C(N)=N3)n2)nc1] | 0.096 |
| 5 | 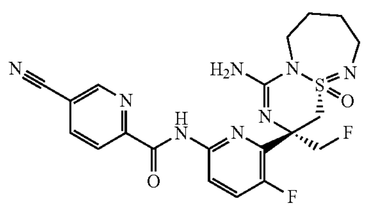 [SMILES: N#Cc1ccc(C(=O)Nc2ccc(F)c([C@]3(CF)C[S@@]4(=O)=NCCCCN4C(N)=N3)n2)nc1] | 0.028 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the Following Composition are Manufactured in the Usual Manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the Following Composition are Manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

19

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the Following Composition are Manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection Solutions of the Following Composition are Manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the Following Composition are Manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

LC-MS (ESI, positive or negative ion) data were recorded on Waters UPLC-MS Systems equipped with Waters Acquity, a CTC PAL auto sampler and a Waters SQD single quadrupole mass spectrometer using ES ionization modes (positive and/or negative). The separation was achieved on a Zorbax Eclipse Plus C18 1.7 µm 2.1×30 mm column at 50° C.; A=0.01% formic acid in water, B=acetonitrile at flow 1; gradient: 0 min 3% B, 0.2 min 3% B, 2 min 97% B, 1.7 min 97% B, 2.0 min 97% B. The injection volume was 2 µL. MS (ESI, positive or negative ion): FIA (flow injection analysis)-MS were recorded on an AppliedBiosystem API150 mass spectrometer. Sample introduction was made with a CTC PAL auto sampler and a Shimadzu LC-10ADVP Pump. The samples were directly flushed to the ESI source of the mass spectrometer with a flow 50 µL/min of a mixture of acetonitrile and 10 mM ammonium acetate (1:1) without a column. The injection volume was 2 µL.

General

Abbreviations:

Boc=tert-Butoxycarbonyl, DCM=dichloromethane, EDC.HCl=N-(3-dimethylaminopropyl)-N'-ethylcarbodiimide hydrochloride, EtOAc=Ethyl acetate, HCl=hydrogen chloride, HPLC=high performance liquid chromatography, LDA=lithium diisopropylamide, MS=mass spectrum, THF=tetrahydrofuran, and T3P=2,4,6-Tripropyl-1,3,5,2,4,6-trioxatriphosphorinane-2,4,6-trioxide.

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Synthesis of the Intermediate Sulfinyl Imines A4

A4a (R$^3$=Me): (R,E)-N-(1-(6-Bromo-3-fluoro-4-(triethylsilyl)pyridin-2-yl)ethylidene)-2-methylpropane-2-sulfinamide

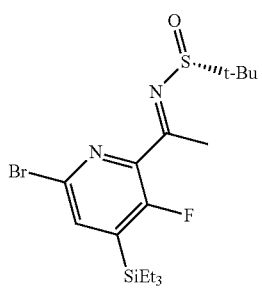

To a solution of 1-(6-bromo-3-fluoro-4-(triethylsilyl)pyridin-2-yl)ethanone, prepared according to Badiger, S. et al., int. patent application WO 2012095469A1, (8.13 g) in THF (59 ml) was added subsequently at 22° C. (R)-(+)-tert-butylsulfinamide (3.26 g) and titanium(IV)ethoxide (11.2 g) and the solution was stirred at 60° C. for 6 h. The mixture was cooled to 22° C., treated with brine, the suspension was stirred for 10 min and filtered over dicalite. The layers were separated, the aqueous layer was extracted with ethyl acetate, the combined organic layers were washed with water, dried and evaporated. The residue was purified by flash chromatography (SiO$_2$, n-heptane/EtOAc, 5:1) to give the title compound (7.5 g, 70%) as a yellow oil. MS (ESI): m/z=435.3, 437.3 [M+H]$^+$.

A4b (R$^3$=CH$_2$F): (R,E)-N-(1-(6-bromo-3-fluoro-4-(triethylsilyl)pyridin-2-yl)-2-fluoroethylidene)-2-methylpropane-2-sulfinamide

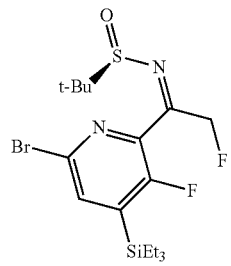

Step I: To a solution of diisopropylamine (3.55 g, 5.00 ml, 35.1 mmol, Eq: 1.1) in tetrahydrofuran (80 ml) was added dropwise at −40° C. under inert atmosphere n-BuLi (1.6 M in hexane) (21.9 ml, 35.1 mmol, Eq: 1.1). After complete addition the solution was allowed to warm to −10° C. and stirred for 10 minutes. The mixture was again cooled to −78° C. and a solution of 2-bromo-5-fluoro-4-(triethylsilyl)pyridine (9.26 g, 31.9 mmol, Eq: 1.00), prepared according to Badiger, S. et al., int. patent application WO 2012095469A1, in tetrahydrofuran (20 ml) was added dropwise while internal temperature was held below −70° C. The yellow solution was stirred at −78° C. for 1 hour while color changed to dark red. Then was added dropwise methyl 2-fluoroacetate (3.52 g, 38.3 mmol, Eq: 1.2). The mixture was warmed to −10° C. within 30 min and then quenched by pouring the mixture onto sat. NH$_4$Cl/1 M HCl. The mixture was extracted twice with EtOAc, dried over Na$_2$SO$_4$, filtered and evaporated to give 1-(6-bromo-3-fluoro-4-(triethylsilyl)pyridin-2-yl)-2-fluoroethanone (11.03 g, 31.5 mmol, 98.7% yield) as a yellow oil which was used without further purification. MS (ESI): m/z=350.3, 352.3 [M+H]$^+$.

Step 2: To a solution of 1-(6-bromo-3-fluoro-4-(triethylsilyl)pyridin-2-yl)-2-fluoroethanone (10.98 g, 28.2 mmol, Eq: 1.00) in THF (100 ml) was added at 23° C. (R)-(+)-2-methylpropane-2-sulfinamide (6.28 g, 50.8 mmol, Eq: 1.8) and titanium(IV) ethoxide (29.0 g, 26.8 ml, 127 mmol, Eq: 4.5). The dark red reaction solution was stirred at 23° C. for 16 hours. 200 ml of water and 200 ml of ethyl acetate were added to the reaction mixture. After stirring for 10 min the slurry was filtered off through a pad of dicalite. The organic layer was separated and washed with water and brine. The aqueous layers were reextracted with ethyl acetate (100 ml). The combined organic extracts were dried over Na$_2$SO$_4$, filtered and evaporated to give a brown oil. The residue was purified by flash chromatography (70 g silica gel, 0-30% EtOAc in heptane) to give (R,E)-N-(1-(6-bromo-3-fluoro-4-(triethylsilyppyridin-2-yl)-2-fluoroethylidene)-2-methylpropane-2-sulfinamide (7.88 g, 17.4 mmol, 61.6% yield) as a yellow oil. MS (ESI): m/z=453.3, 455.6 [M+H]$^+$.

A4c (R$^3$=CHF$_2$): (S,E)-N-(1-(6-bromo-3-fluoro-4-(triethylsilyl)pyridin-2-yl)-2,2-difluoroethylidene)-2-methylpropane-2-sulfinamide

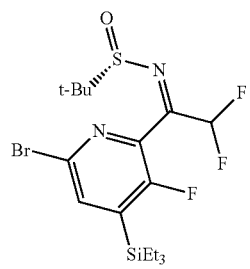

Step 1: A solution of diisopropylamine (3.45 g, 4.86 ml, 34.1 mmol, Eq: 1.10) and THF (90 ml) was cooled to −78° C. n-BuLi (1.6 M in hexane) (21.3 ml, 34.1 mmol, Eq: 1.10) was added dropwise. After complete addition the solution was allowed to warm to −10° C. and stirred for 20 minutes. The mixture was again cooled to −78° C. 2-bromo-5-fluoro-4-(triethylsilyl)pyridine (9 g, 31.0 mmol, Eq: 1.00), prepared according to Badiger, S. et al., int. patent application WO 2012095469A1, was added dropwise at max. −60° C. The yellow solution was stirred at −78° C. for 2 hours while color changed to dark red. Then ethyl difluoroacetate (4.62 g, 3.72 ml, 37.2 mmol, Eq: 1.20) was added dropwise. The mixture was warmed to −10° C. and then quenched by pouring the mixture onto 1 M HCl. The mixture was extracted with EtOAc twice, dried on $Na_2SO_4$, filtered and evaporated. The residue was purified by flash chromatography (silica gel, 70 g, 0-30% EtOAc in heptane) to give 1-(6-bromo-3-fluoro-4-(triethylsilyl)pyridin-2-yl)-2,2-difluoroethanone (3.75 g, 10.2 mmol, 32.8% yield) as a light brown oil.

Step 2: To a solution of 1-(6-bromo-3-fluoro-4-(triethylsilyl)pyridin-2-yl)-2,2-difluoroethanone (3.75 g, 10.2 mmol, Eq: 1.00) in tetrahydrofuran (40.7 ml) was added at rt (S)-(−)-2-methylpropane-2-sulfinamide (2.22 g, 18.3 mmol, Eq: 1.8) and titanium(IV) ethoxide (6.97 g, 6.33 ml, 30.5 mmol, Eq: 3.0). The reaction mixture was stirred at 23° C. for 16 hours and 3 hours at 60° C. 100 ml of water and 100 ml of ethyl acetate were added to the reaction mixture. After stirring for 10 min the slurry was filtered off through a pad of dicalite. The organic layer was separated and washed with water and brine. The aqueous layers were reextracted with ethyl acetate (100 ml). The combined organic extracts were dried over $Na_2SO_4$, filtered and evaporated to give a brown oil. The residue was purified by chromatography (silica gel, 50 g, 0-30% EtOAc in heptane) to give (S,E)-N-(1-(6-bromo-3-fluoro-4-(triethylsilyl)pyridin-2-yl)-2,2-difluoroethylidene)-2-methylpropane-2-sulfinamide (2.73 g, 5.79 mmol, 56.9% yield) as a yellow oil. MS (ESI): m/z=471.1, 473.3 $[M+H]^+$.

Synthesis of the Intermediate Sulfinamide B3
B3a: N-allylmethanesulfinamide

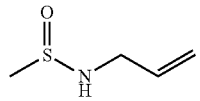

Step 1: A solution of 1,2-dimethyldisulfane (79.6 g, 75 ml, 846 mmol, Eq: 1.00) in acetic acid (102 g, 96.7 ml, 1.69 mol, Eq: 2) was cooled to −20° C. (mixture solidified), start dropwise addition of sulfuryl dichloride (354 g, 212 ml, 2.62 mol, Eq: 3.1) (after 1-2 ml it forms an orange solution). After complete addition stirring was continued at −20° C. for 1.5 h. Removed the cooling bath and let the reaction reach ambient temperature (gas evolution). Stirring was continued at 35° C. for 1 h. Removed the acetyl chloride at 40° C. and 150 mbar at the rotary evaporator and the residue was purified by distillation (bp. 55° C. at 53 mbar) to give the methanesulfinic chloride (144.3 g, 1.46 mol, 86.6% yield) as a light yellow liquid.

Step 2: To a solution of prop-2-en-1-amine (17.4 g, 22.9 ml, 304 mmol, Eq: 3.00) in diethyl ether (312 ml) was added at −78° C. a solution of methanesulfinic chloride (10 g, 101 mmol, Eq: 1.00) in diethyl ether (37.5 ml) dropwise. The reaction mixture was allowed to warm up to 0° C. and was stirred for 1 h to give a suspension. To the suspension were added three spoons of $Na_2SO_4$, filtered and evaporated to give N-allylmethanesulfinamide (10.73 g, 90.0 mmol, 88.7% yield) as a colorless liquid which was used without further purification. MS (ESI): m/z=120.0 $[M+H]^+$.

Synthesis of the Intermediate Sulfinamide B4
B4a: 2-[(2,4-dimethoxyphenyl)methyl]-1-methyl-1λ⁶-thia-2,7-diazacyclohept-7-ene 1-oxide

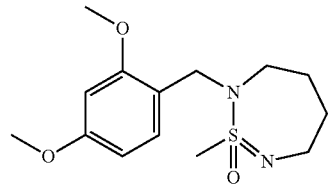 [SMILES: COc1ccc(CN2CCCCN=S2(C)=O)c(OC)c1]

Step 1: To a solution of 2,4-dimethoxybenzaldehyde (7.86 g, 47.3 mmol, Eq: 1.00) and prop-2-en-1-amine (3.24 g, 4.26 ml, 56.8 mmol, Eq: 1.2) in 1,2-dichloroethane (100 ml) was added at 23° C. sodium triacetoxyborohydride (18.0 g, 85.1 mmol, Eq: 1.8) portionwise. The resulting mixture was stirred at 23° C. for 16 hours. The reaction mixture was extracted with 1 N NaOH and DCM twice. The combined organic extracts were dried over $Na_2SO_4$, filtered and evaporated to give a colorless oil (12.5 g, 128%). The residue was purified by chromatography (70 g silica gel, 0-100% ethyl acetate in heptane) to give N-(2,4-dimethoxybenzyl)prop-2-en-1-amine (6.1 g, 29.4 mmol, 62.2% yield) as a colorless oil. MS (ESI): m/z=208.1 $[M+H]^+$.

Step 2: To a solution of N-allylmethanesulfinamide (4 g, 33.6 mmol, Eq: 1.00) in dichloromethane (270 ml) was added in the dark at −78° C. tert-butyl hypochlorite (3.83 g, 3.99 ml, 35.2 mmol, Eq: 1.05) (1.91 g, 1.99 ml, 17.6 mmol, Eq: 1.05). After stirring at −78° C. for 30 min a solution of N-(2,4-dimethoxybenzyl)prop-2-en-1-amine (8.35 g, 40.3 mmol, Eq: 1.2) and triethylamine (5.09 g, 7.02 ml, 50.3 mmol, Eq: 1.5) in dichloromethane (90.0 ml) was dropwise added within 10 min. The cooling bath was removed and the mixture was stirred while warming up to ambient temperature. After 2 h the mixture was poured onto 1 M HCl and extracted twice with DCM. The combined organic layers were dried over $Na_2SO_4$, filtered and evaporated to give the crude N,N'-diallyl-N-(2,4-dimethoxybenzyl)methanesulfonimidamide (10.67 g, 32.9 mmol, 98.0% yield) which was used without further purification. MS (ESI): m/z=325.2 $[M+H]^+$.

Step 3: To a solution of N,N'-diallyl-N-(2,4-dimethoxybenzyl)methanesulfonimidamide (10.67 g, 32.9 mmol, Eq: 1.00) in dichloromethane (400 ml) was added under argon tricyclohexylphosphine[1,3-bis(2,4,6-trimethylphenyl)-4,5-dihydroimidazol-2-ylidene]ruthenium (II) (Grubbs II, Grubbs $2^{nd}$ generation catalyst) (96.8 mg, 114 µmol, Eq: 0.05). The reaction mixture was stirred at reflux (50° C. oilbath) for 2 hours. The mixture was evaporated and the residue was purified by column chromatography (200 g silica gel, 0-10% methanol in ethyl acetate) to give 2-[(2,4-dimethoxyphenyl)methyl]-1-methyl-1λ⁶-thia-2,7-diazacyclohepta-4,7-diene 1-oxide (6.25 g, 21.1 mmol, 64.1% yield) as a brown oil. MS (ESI): m/z=297.2 $[M+H]^+$.

Step 4: To a solution of 2-[(2,4-dimethoxyphenyl)methyl]-1-methyl-1λ⁶-thia-2,7-diazacyclohepta-4,7-diene 1-oxide (6.25 g, 21.1 mmol, Eq: 1.00) in ethyl acetate (350 ml) was added under argon 10% Pd/C (1.12 g, 1.05 mmol, Eq: 0.05). The black suspension was set under hydrogen and was stirred for 2 hours. Added again 700 mg of 10% Pd/C and was stirred again for 1 h. Then the suspension was set again under argon and the reaction mixture was filtered and evaporated to give. The crude material was purified by flash chromatography (50 g silica gel, 0-20% methanol in ethyl acetate) to give 2-[(2,4-dimethoxyphenyl)methyl]-1-methyl-1λ$^6$-thia-2,7-diazacyclohept-7-ene 1-oxide (6.18 g, 20.7 mmol, 98.2% yield) as a brown oil. MS (ESI): m/z=299.3 [M+H]$^+$.

Synthesis of the Intermediates A5

A5a (R$^3$=Me): 2-Methyl-propane-2-sulfinic acid {(R)-1-(6-bromo-3-fluoro-4-triethylsilyl-pyridin-2-yl)-2-[(R/S)-2-(2,4-dimethoxy-benzyl)-1-oxo-3,4,5,6-tetrahydro-2H-1λ$^6$-[1,2,7]thiadiazepin-1-yl]-1-methyl-ethyl}-amide

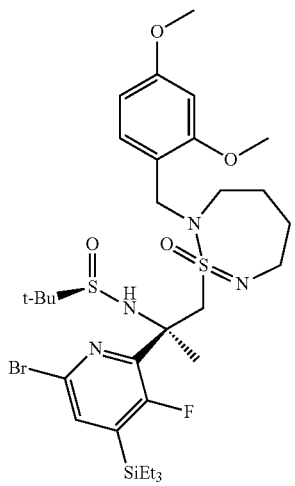

To a solution of 2-[(2,4-dimethoxyphenyl)methyl]-1-methyl-1λ$^6$-thia-2,7-diazacyclohept-7-ene 1-oxide (1.92 g, 6.43 mmol, Eq: 2.0) in tetrahydrofuran (30 ml) at −75° C. was dropwise added n-BuLi (1.6 M in hexane) (3.98 ml, 6.37 mmol, Eq: 1.98). The clear solution was stirred at −50° C. for 2 hours. Then a solution of (R,E)-N-(1-(6-bromo-3-fluoro-4-(triethylsilyl)pyridin-2-yl)ethylidene)-2-methyl-propane-2- sulfinamide (1.4 g, 3.21 mmol, Eq: 1.00) in tetrahydrofuran (10 ml) was added at −75° C. dropwise. The reaction mixture was stirred at −50° C. for 3 hours, and quenched at −75° C. with 10 ml of sat. NH$_4$Cl-sol. and 30 ml of water, followed by extraction with ethyl acetate (2×50 ml). The combined organic extracts were dried over Na$_2$SO$_4$, filtered and evaporated to give orange oil. The residue was purified by flash chromatography (50 g silica gel, 0-80% EtOAc in heptane) to give the 2-methyl-propane-2-sulfinic acid {(R)-1-(6-bromo-3-fluoro-4-triethylsilyl-pyridin-2-yl)-2-[(R/S)-2-(2,4-dimethoxy-benzyl)-1-oxo-3,4,5,6-tetrahydro-2H-1λ$^6$-[1,2,7]thiadiazepin-1-yl]-1-methyl-ethyl}-amide as a 1:1 mixture of 2 epimers. MS (ESI): m/z=733.2; 735.4 [M+H]$^+$.

A5b (R$^3$=CH$_2$F): 2-Methyl-propane-2-sulfinic acid {(S)-1-(6-bromo-3-fluoro-4-triethylsilanyl-pyridin-2-yl)-1-[(S/R)-2-(2,4-dimethoxy-benzyl)-1-oxo-3,4,5,6-tetrahydro-2H-1λ$^6$-[1,2,7]thiadiazepin-1-ylmethyl]-2-fluoro-ethyl}-amide

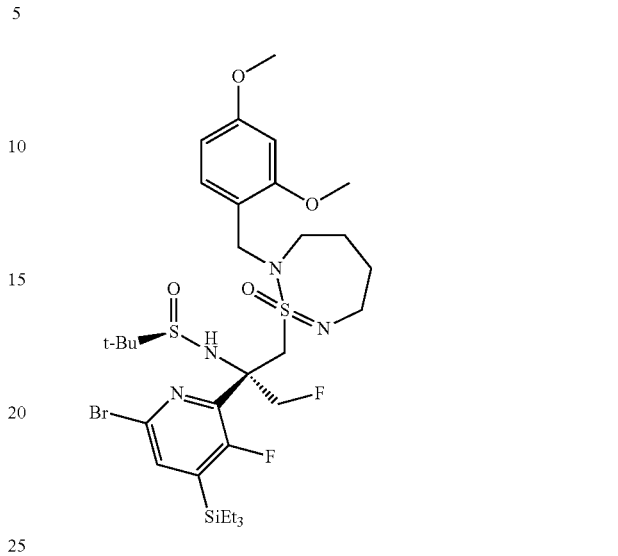

Prepared from 2-[(2,4-dimethoxyphenyl)methyl]-1-methyl-1λ$^6$-thia-2,7-diazacyclohept-7-ene 1-oxide (2.6 g, 8.71 mmol, Eq: 1.98) and (R,E)-N-(1-(6-bromo-3-fluoro-4-(triethylsilyl)pyridin-2-yl)-2-fluoroethylidene)-2- methyl-propane-2-sulfinamide (2 g, 4.41 mmol, Eq: 1.00) according to the procedure described for intermediate A5a to give the 2-methyl-propane-2-sulfinic acid {(S)-1-(6-bromo-3-fluoro-4-triethylsilanyl-pyridin-2-yl)-1-[(S/R)-2-(2,4-dimethoxy-benzyl)-1-oxo-3,4,5,6-tetrahydro-2H- 1λ$^6$-[1,2,7]thiadiazepin-1-ylmethyl]-2-fluoro-ethyl}-amide (440 mg, 585 μmol, 13.3% yield) as a yellow solid as a 1:1 mixture of 2 epimers. MS (ESI): m/z=751.2; 753.3 [M+H]$^+$.

Synthesis of the Intermediates A6

A6a (R$^3$=Me): 2-Methyl-propane-2-sulfinic acid {(R)-1-(6-bromo-3-fluoro-pyridin-2-yl)-2-[(R/S)-2-(2,4-dimethoxy- benzyl)-1-oxo-3,4,5,6-tetrahydro-2H-1λ$^6$-[1,2,7] thiadiazepin-1-yl]-1-methyl-ethyl}-amide

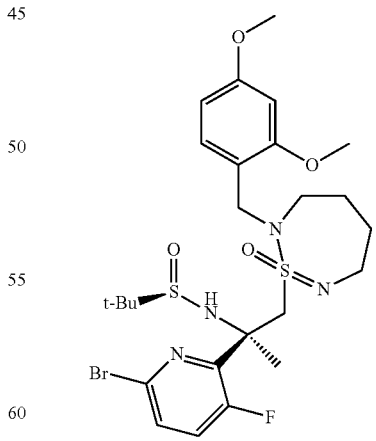

To a solution of 2-methyl-propane-2-sulfinic acid {(R)-1-(6-bromo-3-fluoro-4-triethylsilyl-pyridin-2-yl)-2-[(R/S)-2-(2,4- dimethoxy-benzyl)-1-oxo-3,4,5,6-tetrahydro-2H-1λ$^6$-[1,2,7]thiadiazepin-1-yl]-1-methyl-ethyl}-amide (3.82 g, 5.2 mmol, Eq: 1.00) in tetrahydrofuran (50 ml) and DMF (10 ml) was added at 23° C. acetic acid (313 mg, 298 μl, 5.21 mmol, Eq: 1.0) and dry potassium fluoride (302 mg, 5.21 mmol, Eq: 1.0). The reaction mixture was stirred at 23° C. for 3 hours. The reaction mixture was evaporated, then extracted twice with ethyl acetate/NaHCO$_3$, washed the organic layers with brine, dried over Na$_2$SO$_4$, filtered and evaporated to the crude 2-methyl-propane-2-sulfinic acid {(R)-1-(6-bromo-3-fluoro-pyridin-2-yl)-2-[(R/S)-2-(2,4-dimethoxy-benzyl)-1-oxo-3,4,5,6-tetrahydro-2H-1λ$^6$-[1,2,7]thiadiazepin-1-yl]-1-methyl-ethyl}-amide (2.88 g, 4.64 mmol, 89.3% yield) as a 1:1 mixture of epimers which was used without further purification. MS (ESI): m/z=619.3; 621.5 [M+H]$^+$.

A6b (R$^3$=CH$_2$F): 2-Methyl-propane-2-sulfinic acid {(S)-1-(6-bromo-3-fluoro-pyridin-2-yl)-2-[(S/R)-2-(2,4-dimethoxy-benzyl)-1-oxo-3,4,5,6-tetrahydro-2H-1λ$^6$-[1,2,7]thiadiazepin-1-ylmethyl]-2-fluoro-ethyl}-amide

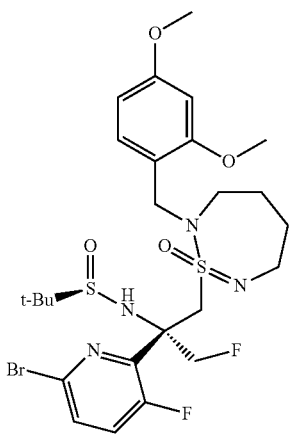 [SMILES: COc1ccc(CN2CCCCN=S2(=O)C[C@](CF)(N[S@](=O)C(C)(C)C)c2nc(Br)ccc2F)c(OC)c1]

Prepared from 2-methyl-propane-2-sulfinic acid {(S)-1-(6-bromo-3-fluoro-4-triethylsilanyl-pyridin-2-yl)-1-[(S/R)-2-(2,4-dimethoxy-benzyl)-1-oxo-3,4,5,6-tetrahydro-2H-1λ$^6$-[1,2,7]thiadiazepin-1-ylmethyl]-2-fluoro-ethyl}-amide (780 mg, 1.04 mmol, Eq: 1.00) according to the procedure described for intermediate A6a to give the 2-methyl-propane-2-sulfinic acid {(S)-1-(6-bromo-3-fluoro-pyridin-2-yl)-2-[(S/R)-2-(2,4-dimethoxy-benzyl)-1-oxo-3,4,5,6-tetrahydro-2H-1λ$^6$-[1,2,7]thiadiazepin-1-ylmethyl]-2-fluoro-ethyl}-amide (660 mg, 1.04 mmol, 99.8% yield) as a light yellow oil as a 1:1 mixture of epimers which was used without further purification. MS (ESI): m/z=637.2; 639.5 [M+H]$^+$.

Synthesis of the Intermediates A7

A7a (R$^3$=Me): (2R)-2-(6-bromo-3-fluoropyridin-2-yl)-1-[(1R/S)-1-oxo-1λ$^6$-thia-2,7-diazacyclohept-7-en-1-yl]propan-2-amine

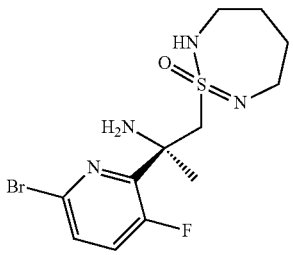 [SMILES: C[C@](N)(CS1(=O)=NCCCCN1)c1nc(Br)ccc1F]

To a solution of 2-methyl-propane-2-sulfinic acid {(R)-1-(6-bromo-3-fluoro-pyridin-2-yl)-2-[(R/S)-2-(2,4-dimethoxy-benzyl)-1-oxo-3,4,5,6-tetrahydro-2H-1λ$^6$-[1,2,7]thiadiazepin-1-yl]-1-methyl-ethyl}-amide (2.88 g, 4.64 mmol, Eq: 1.0) in THF (10 ml) was added at 23° C. HCl (4 N in dioxane) (1.74 ml, 6.97 mmol, Eq: 1.5). After stiffing for 1 h the reaction mixture was evaporated. Then TFA (26.5 g, 17.9 ml, 232 mmol, Eq: 100) was added and stirring continued at 23° C. for 18 h. The dark red reaction solution was evaporated, extracted with sat. NaHCO$_3$-sol./ethyl acetate, washed the organic layers with brine, dried over Na$_2$SO$_4$, filtered and evaporated. The residue was purified by flash chromatography (20 g silica gel, 0-10% MeOH in CH$_2$Cl$_2$) to give the (2R)-2-(6-bromo-3-fluoropyridin-2-yl)-1-[(1R/S)-1-oxo-1λ$^6$-thia-2,7-diazacyclohept-7-en-1-yl]propan-2-amine (700 mg, 1.92 mmol, 82.5% yield) as a light brown solid (1:1 mixture of epimers). MS (ESI): m/z=365.2; 367.4 [M+H]$^+$.

A7b (R$^3$=CH$_2$F): (2S)-2-(6-Bromo-3-fluoropyridin-2-yl)-1-fluoro-3-[(1S/R)-1-oxo-1λ$^6$-thia-2,7-diazacyclohept-7-en-1-yl]propan-2-amine

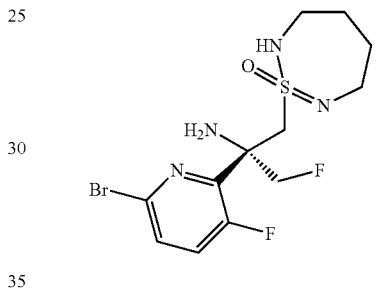

Prepared from 2-methyl-propane-2-sulfinic acid {(S)-1-(6-bromo-3-fluoro-pyridin-2-yl)-2-[(S/R)-2-(2,4-dimethoxy-benzyl)-1-oxo-3,4,5,6-tetrahydro-2H-1λ$^6$-[1,2,7]thiadiazepin-1-ylmethyl]-2-fluoro-ethyl}-amide (650 mg, 1.02 mmol, Eq: 1.00) according to the procedure described for intermediate A7a to give the (2S)-2-(6-bromo-3-fluoropyridin-2-yl)-1-fluoro-3-[(1S/R)-1-oxo-1λ$^6$-thia-2,7-diazacyclohept-7-en-1-yl]propan-2-amine (320 mg, 835 μmol 81.9% yield) as a white solid (1:1 mixture of epimers). MS (ESI): m/z=383.2; 385.4 [M+H]$^+$.

Synthesis of the Intermediates A8 and A9

A9a (R$^3$=Me): N—R3R,4aR)-3-(6-Bromo-3-fluoro-pyridin-2-yl)-3-methyl-4a-oxo-3,4,6,7,8,9-hexahydro-4aλ$^6$-thia-2,5,9a-triaza-benzocyclohepten-1-A-benzamide A9b (R$^3$=Me): N—R3R,4aS)-3-(6-Bromo-3-fluoro-pyridin-2-yl)-3-methyl-4a-oxo-3,4,6,7,8,9-hexahydro-4aλ$^6$-thia-2,5,9a-triaza-benzocyclohepten-1-A-benzamide

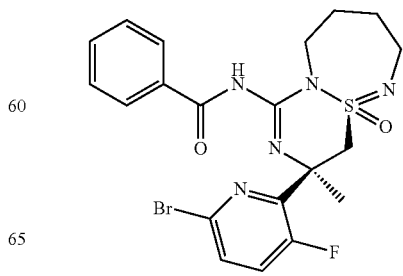

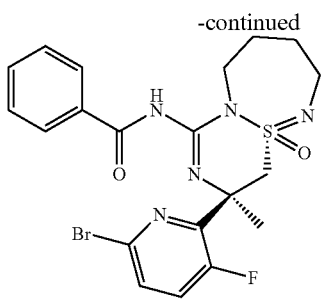

Step 1: To a solution of a mixture of (R)-1-(6-Bromo-3-fluoro-pyridin-2-yl)-1-methyl-2-((R/S)-1-oxo-3,4,5,6-tetrahydro-2H-1λ⁶-[1,2,7]thiadiazepin-1-yl)-ethylamine (690 mg, 1.89 mmol, Eq: 1.00) in tetrahydrofuran (34.5 ml) was added at 23° C. benzoyl isothiocyanate (339 mg, 279 µl 2.08 mmol, Eq: 1.1). After stirring for 1 hour at 23° C. the light yellow solution was evaporated to give the intermediate thiourea A8a/b which was used directly in the next step.

Step 2: The intermediate thiourea A8a/b from step 1 was dissolved in acetonitrile (34.5 ml) and EDC.HCl (543 mg, 2.83 mmol, Eq: 1.5) was added and the reaction mixture was stirred at 80° C. for 2 hours. The light yellow solution was evaporated and the residue was directly purified by chromatography (20 g silica gel, 0-50% EtOAc in heptane) to give N-[(3R,4aR)-3-(6-bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-benzamide (240 mg, 485 µmol, 25.7% yield) as the faster eluting isomer and N-[(3R,4aS)-3-(6-bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-benzamide (220 mg, 445 µmol, 23.6% yield) as the slower eluting isomer. MS (ESI): m/z=494.3; 496.2 [M+H]⁺.

A9c (R³=CH₂F): N-[(1R/S,10S)-10-(6-bromo-3-fluoro-pyridin-2-yl)-10-(fluoromethyl)-1-oxo-1λ⁶-thia-2,7,9-triazabicyclo[5.4.0]undeca-1,8-dien-8-yl]benzamide

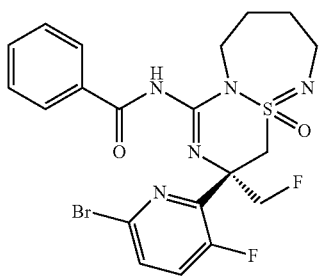 [SMILES: O=C(NC1=N[C@](CF)(c2nc(Br)ccc2F)CS2(=O)=NCCCCN12)c1ccccc1]

Prepared in two steps from (2S)-2-(6-bromo-3-fluoropyridin-2-yl)-1-fluoro-3-[(1S/R)-1-oxo-1λ⁶-thia-2,7-diazacyclohept-7-en-1-yl]propan-2-amine (320 mg, 835 µmol, Eq: 1.00) according to the procedure described for intermediates A9a/b to give the N-[(1R/S,10S)-10-(6-bromo-3-fluoropyridin-2-yl)-10-(fluoromethyl)-1-oxo-1λ⁶-thia-2,7,9-triazabicyclo[5.4.0]undeca-1,8-dien-8-yl]benzamide (332 mg, 648 µmol, 77.6% yield) as a white foam (1:1 mixture of epimers). MS (ESI): m/z=512.2; 514.3 [M+H]⁺.

Synthesis of the Intermediates A10

A10a (R³=Me): (3R,4aR)-3-(6-Bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-carbamic acid tert-butyl Ester

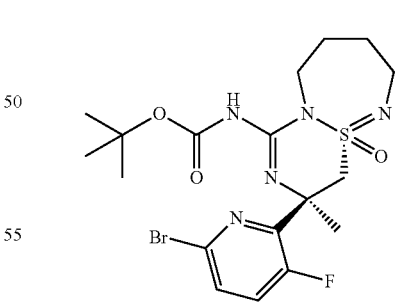

Step 1: To a solution of N-[(3R,4aR)-3-(6-bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-benzamide (230 mg, 465 µmol, Eq: 1.00) in tetrahydrofuran (4 ml) was added at 23° C. triethylamine (104 mg, 143 µl, 1.02 mmol, Eq: 2.2) and DMAP (11.4 mg, 93.0 µmol, Eq: 0.2) followed by the addition of Boc₂O (223 mg, 1.02 mmol, Eq: 2.2). The reaction mixture was stirred at 23° C. for 4 hours. Evaporated all volatiles to give the intermediate N-Boc/N-benzoyl compound which was used directly in the next step.

Step 2: The intermediate N-Boc/N-benzoyl compound from step 1 was dissolved in methanol (2 ml) and ammonia (7 N in methanol) (1.66 ml, 11.6 mmol, Eq: 25) was added and the mixture was stirred at 23° C. for 30 min. Evaporation of all volatiles and the residue was purified by chromatography (20 g silica gel, 0-50% EtOAc in heptane) to give (3R,4aR)-3-(6-bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-carbamic acid tert-butyl ester (168 mg, 343 µmol, 73.6% yield) as a white foam. MS (ESI): m/z=490.1; 492.2 [M+H]⁺.

A10b (R³=Me): (3R,4aS)-3-(6-Bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-carbamic acid tert-butyl ester Step 1: To a solution of N-[(3R,4aS)-3-(6-bromo-3-fluoro-pyridin-2-yl)-3-methyl-4a-oxo-3,4,6,7,8,9-hexahydro-4aλ⁶-thia-2,5,9a-triaza-benzocyclohepten-1-yl]-benzamide (253 mg, 512 µmol, Eq: 1.00) in tetrahydrofuran (4 ml) was added at 23° C. triethylamine (114 mg, 157 µl, 1.13 mmol, Eq: 2.2) and DMAP (12.5 mg, 102 µmol, Eq: 0.2) followed by the addition of Boc₂O (246 mg, 1.13 mmol, Eq: 2.2). The reaction mixture was stirred at 23° C. for 4 hours.

Evaporated all volatiles to give the intermediate N-Boc/N-benzoyl compound which was used directly in the next step.

Step 2: The intermediate N-Boc/N-benzoyl compound from step 1 was dissolved in methanol (2 ml) and ammonia (7 N in methanol) (1.66 ml, 11.6 mmol, Eq: 25) was added and the mixture was stirred at 23° C. for 30 min. Evaporation of all volatiles and the residue was purified by chromatography (20 g silica gel, 0-50% EtOAc in heptane) to give (3R,4aS)-3-(6-bromo-3-fluoro-pyridin-2-yl)-3-methyl-4a-oxo-3,4,6,7,8,9-hexahydro-4a$\lambda^6$-thia-2,5,9a-triaz a-benzocyclohepten-1-yl]-carbamic acid tert-butyl ester (213 mg, 434 μmol, 84.9% yield) as a white foam. MS (ESI): m/z=490.1; 492.2 [M+H]$^+$.

A10c (R$^3$=CH$_2$F): tert-butyl N-[(1R/S,10S)-10-(6-bromo-3-fluoropyridin-2-yl)-10-(fluoromethyl)-1-oxo-1$\lambda^6$-thia-2,7,9-triazabicyclo[5.4.0]undeca-1,8-dien-8-yl]carbamate

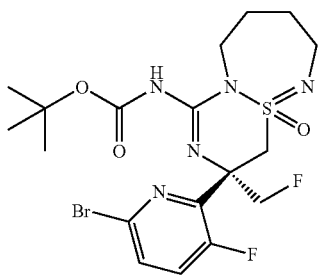 [SMILES: CC(C)(C)OC(=O)NC1=N[C@](CF)(c2nc(Br)ccc2F)CS2(=O)=NCCCCN12]

Prepared from N-[(1R/S,10S)-10-(6-bromo-3-fluoropyridin-2-yl)-10-(fluoromethyl)-1-oxo-1$\lambda^6$-thia-2,7,9-triazabicyclo[5.4.0]undeca-1,8-dien-8-yl]benzamide (328 mg, 640 μmol, Eq: 1.00) according to the procedure described for intermediates A10 to give the tert-butyl N-[(1R/S,10S)-10-(6-bromo-3-fluoropyridin-2-yl)-10- (fluoromethyl)-1-oxo-1$\lambda^6$-thia-2,7,9-triazabicyclo[5.4.0]undeca-1,8-dien-8-yl] carbamate (242 mg, 476 μmol, 74.4% yield) as a white foam (1:1 mixture of epimers). MS (ESI): m/z=508.3; 510.2 [M+H]$^+$.

Synthesis of the Intermediate Boc-Aminopyridine A11

A11a (R$^3$=Me): [(3R,4aR)-3-(6-Amino-3-fluoro-pyridin-2-yl)-3-methyl-4a-oxo-3,4,6,7,8,9-hexahydro-4a$\lambda^6$- thia-2,5,9a-triaza-benzocyclohepten-1-yl]-carbamic acid tert-butyl ester

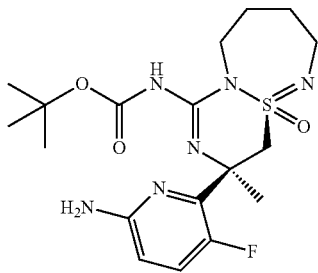 [SMILES: CC(C)(C)OC(=O)NC1=N[C@](C)(c2nc(N)ccc2F)C[S@]2(=O)=NCCCCN12]

To a solution of (3R,4aR)-3-(6-bromo-3-fluoro-pyridin-2-yl)-3-methyl-4a-oxo-3,4,6,7,8,9-hexahydro-4a$\lambda^6$-thia-2,5,9a- triaza-benzocyclohepten-1-yl]-carbamic acid tert-butyl ester (167 mg, 341 μmol, Eq: 1.00) in dioxane (3.00 ml) and water (1.00 ml) was added at 23° C. sodium azide (177 mg, 2.72 mmol, Eq: 8.0) followed by the addition of copper (I) iodide (25.9 mg, 136 μmol, Eq: 0.4), sodium L-ascorbate (13.5 mg, 68.1 μmol, Eq: 0.2) and finally trans-N,N'-dimethylcyclohexane-1,2-diamine (29.1 mg, 32.2 μl, 204 μmol, Eq: 0.6). The dark reaction mixture was stirred at 70° C. for 30 min. The dark green reaction mixture was quenched with sat. NaHCO$_3$-sol., then extracted twice with ethyl acetate. The combined organic layers were dried over Na$_2$SO$_4$, filtered and evaporated to give a brown oil, which was purified by flash chromatography (10 g silica gel; 0-100% ethyl acetate in heptane) to give [(3R,4aR)-3-(6-amino-3-fluoro-pyridin-2-yl)-3-methyl-4a-oxo-3,4,6,7,8,9-hexahydro-4a$\lambda^6$-thia-2,5,9a-triaza-benzocyclohepten-1-yl]-carbamic acid tert-butyl ester (36 mg, 84.4 μmol, 24.8% yield) as a light yellow foam. MS (ESI): m/z=427.4 [M+H]$^+$.

A11b (R$^3$=Me): [(3R,4aS)-3-(6-Amino-3-fluoro-pyridin-2-yl)-3-methyl-4a-oxo-3,4,6,7,8,9-hexahydro-4a$\lambda^6$- thia-2,5,9a-triaza-benzocyclohepten-1-yl]-carbamic acid tert-butyl ester

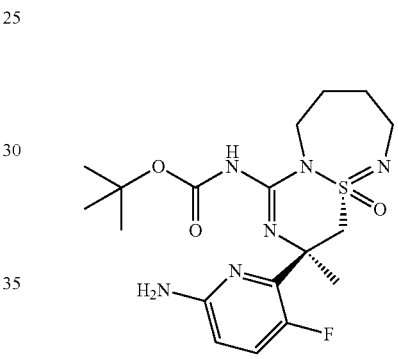

To a solution of [(3R,4aS)-3-(6-bromo-3-fluoro-pyridin-2-yl)-3-methyl-4a-oxo-3,4,6,7,8,9-hexahydro-4a$\lambda^6$-thia-2,5,9a-triaza-benzocyclohepten-1-yl]-carbamic acid tert-butyl ester (213 mg, 434 μmol, Eq: 1.00) in dioxane (3.00 ml) and water (1.00 ml) was added at 23° C. sodium azide (226 mg, 3.47 mmol, Eq: 8.0) followed by the addition of copper(I) iodide (33.1 mg, 174 μmol, Eq: 0.4), sodium L-ascorbate (17.2 mg, 86.9 μmol, Eq: 0.2) and finally trans-N,N'-dimethylcyclohexane-1,2-diamine (37.1 mg, 41.1 μl, 261 μmol, Eq: 0.6). The dark reaction mixture was stirred at 70° C. for 1 h. The dark green reaction mixture was quenched with sat. NaHCO$_3$-sol., then extracted twice with ethyl acetate. The combined organic layers were dried over Na$_2$SO$_4$, filtered and evaporated to give a brown oil, which was purified by flash chromatography (10 g silica gel; 0-20% methanol in dichloromethane) to give [(3R,4aS)-3-(6-amino-3-fluoro-pyridin-2-yl)-3-methyl-4a-oxo-3,4,6,7,8,9-hexahydro-4a$\lambda^6$-thia-2,5,9a-triaza-benzocyclohepten-1-yl]-carbamic acid tert-butyl ester (154 mg, 307 μmol, 70.7% yield) as an off-white solid. MS (ESI): m/z=427.4 [M+H]$^+$.

A11c (R³=CH₂F): tert-butyl N-[(1S,10S)-10-(6-amino-3-fluoropyridin-2-yl)-10-(fluoromethyl)-1-oxo-1λ⁶-thia-2,7,9-triazabicyclo[5.4.0]undeca-1,8-dien-8-yl]carbamate A11d (R³=CH₂F): tert-butyl N-[(1R,10S)-10-(6-amino-3-fluoropyridin-2-yl)-10-(fluoromethyl)-1-oxo-1λ⁶-thia-2,7,9-triazabicyclo[5.4.0]undeca-1,8-dien-8-yl]carbamate

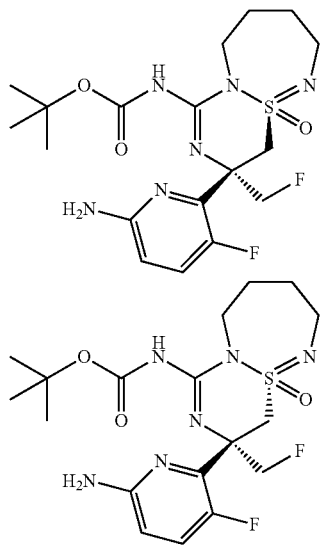

Prepared from to give the tert-butyl N-[(1R/S,10S)-10-(6-bromo-3-fluoropyridin-2-yl)-10-(fluoromethyl)-1-oxo-1λ⁶-thia-2,7,9- triazabicyclo[5.4.0]undeca-1,8-dien-8-yl]carbamate (242 mg, 476 µmol, Eq: 1.00) according to the procedure described for intermediates A11 to give the faster eluting isomer tert-butyl N-[(1S,10S)-10-(6-amino-3-fluoropyridin-2-yl)-10-(fluoromethyl)-1-oxo-1λ⁶-thia-2,7,9- triazabicyclo[5.4.0]undeca-1,8-dien-8-yl]carbamate (61 mg, 137 µmol, 28.8% yield) as a white foam and the slower eluting isomer tert-butyl N-[(1R,10S)-10-(6-amino-3-fluoropyridin-2-yl)-10- (fluoromethyl)-1-oxo-1λ⁶-thia-2,7,9-triazabicyclo[5.4.0]undeca-1,8-dien-8-yl]carbamate (76 mg, 171 µmol, 35.9% yield) as a light yellow solid. MS (ESI): m/z=445.4 [M+H]⁺.

Synthesis of the Intermediate Boc-Amides A12 Deprotected Amides I

General Procedure for the Coupling of the Boc-Aminopyridines A11 with the Acid to the Boc-Amide A12

T3P-method: To a solution of the Boc-aminopyridine A11 (0.10 mmol) and the acid (0.2 mmol) in EtOAc (1.2 ml) was added at 22° C. T3P (50% in EtOAc, 0.09 ml, 0.15 mmol) and stirring was continued 2 h. A further portion of T3P (0.05 ml, 0.08 mmol) was added and stirring was continued for 2 h. The mixture was partitioned between saturated aqueous NaHCO₃ and EtOAc, the organic layer was dried, evaporated and the residue purified by flash chromatography (SiO₂, gradient of EtOAc in heptane) to give the Boc-amide A12.

Ghosez's reagent method: To a suspension of the acid (197 µmol, Eq: 1.5) in dry dichloromethane (1.5 ml) at 0° C. was dropwise added 1-chloro-N,N,2-trimethylpropenylamine (Ghosez's reagent) (52.8 mg, 395 µmol, Eq: 3) and the mixture was stirred at 0° C. for 1 hour. This mixture was then added to a solution of the Boc-aminopyridine A11 (132 µmol, Eq: 1.00) and diisopropylethylamine (51.0 mg, 69.0 µl, 395 µmol, Eq: 3) in dry dichloromethane (1.5 ml) at 0° C. The ice bath was removed and the mixture was stirred 1 to 16 hour(s) at ambient temperature. Evaporated totally at ambient temperature and directly purified by flash chromatography (silica gel, gradient of EtOAc in heptane) to give the Boc-amide A12.

General Procedure for the Deprotection of the Boc-Amide A12 to the Amide I

To a solution of the Boc-amide A12 (0.04 mmol) in dichloromethane (0.5 ml) was added at 22° C. trifluoroacetic acid (1.2 mmol) and stirring was continued for 16 h. The mixture was evaporated, the residue diluted with EtOAc and evaporated again. The residue was triturated with diethyl ether/pentane, the suspension was filtered and the residue dried to give the amide I. Alternative workup to obtain the free base: after stirring for 16 h, all volatiles were removed in vacuum, the residue was partitioned between EtOAc and sat. NaHCO₃-sol., the organic layer was washed with brine and dried over Na₂SO₄. Filtration and removal of the solvent in vacuum left the crude product which was purified by flash chromatography to give the amide I.

A12a (R³=Me): ((3R,4aR)-3-{6-[(5-Cyano-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester

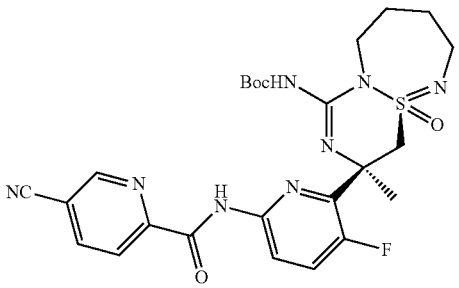

[(3R,4aR)-3-(6-Amino-3-fluoro-pyridin-2-yl)-3-methyl-4a-oxo-3,4,6,7,8,9-hexahydro-4aλ⁶-thia-2,5,9a-triaza- benzocyclohepten-1-yl]-carbamic acid tert-butyl ester A11a (28 mg, 65.6 µmol) was coupled with 5-cyanopicolinic acid according to the Ghosez's reagent-method to give the title compound (64 mg, 69.0 µmol, 105% yield) as a yellow oil which was used without further purification. MS (ESI): m/z=557.5 [M+H]⁺.

A12b (R³=Me): ((3R,4aS)-3-{6-[(5-Cyano-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester

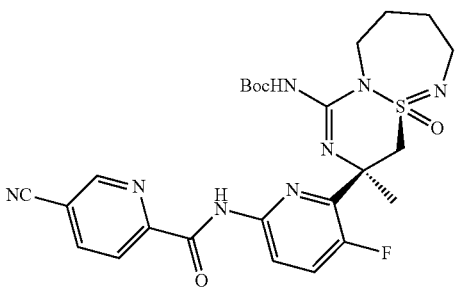 [SMILES: CC(C)(C)OC(=O)NC1=N[C@](C)(c2nc(NC(=O)c3ccc(C#N)cn3)ccc2F)C[S@]2(=O)=NCCCCN12]

[(3R,4aS)-3-(6-Amino-3-fluoro-pyridin-2-yl)-3-methyl-4a-oxo-3,4,6,7,8,9-hexahydro-4aλ⁶-thia-2,5,9a-triaza- benzocyclohepten-1-yl]-carbamic acid tert-butyl ester A11b (71 mg, 166 µmol) was coupled with 5-cyanopicolinic acid according to the Ghosez's reagent-method to give after flash chromatography (SiO₂, gradient of MeOH in DCM, 0 to 20% MeOH) the title compound (144 mg, 186 µmol, 112% yield) as a yellow oil which was used without further purification. MS (ESI): m/z=557.4 [M+H]⁺.

A12c (R³=Me): ((3R,4aS)-3-{6-[(5-Cyano-3-methyl-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester

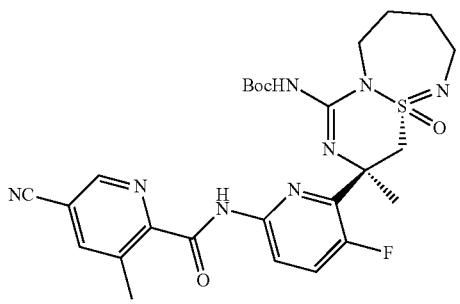 [SMILES: Cc1cc(C#N)cnc1C(=O)Nc1ccc(F)c([C@]2(C)C[S@@]3(=O)=NCCCCN3C(NC(=O)OC(C)(C)C)=N2)n1]

[(3R,4aS)-3-(6-Amino-3-fluoro-pyridin-2-yl)-3-methyl-4a-oxo-3,4,6,7,8,9-hexahydro-4aλ⁶-thia-2,5,9a-triaza- benzocyclohepten-1-yl]-carbamic acid tert-butyl ester A11b (35 mg, 82.1 µmol) was coupled with 5-cyano-3-methylpicolinic acid according to the Ghosez's reagent-method to give the crude title compound (70 mg, 85.9 µmol, 105% yield) as a yellow oil which was used without further purification. MS (ESI): m/z=571.3 [M+H]⁺.

A12d (R³=CH₂F): tert-butyl N-[(1S,10S)-10-[6-[(5-cyanopyridine-2-carbonyl)amino]-3-fluoropyridin-2-yl]-10-(fluoromethyl)-1-oxo-1λ⁶-thia-2,7,9-triazabicyclo[5.4.0]undeca-1,8-dien-8-yl]carbamate

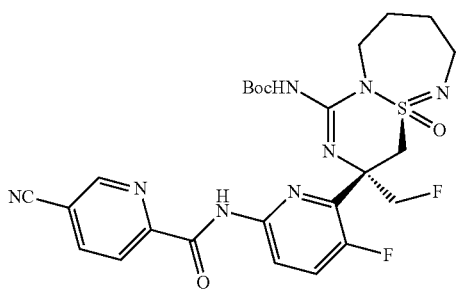 [SMILES: CC(C)(C)OC(=O)NC1=N[C@](CF)(c2nc(NC(=O)c3ccc(C#N)cn3)ccc2F)C[S@]2(=O)=NCCCCN12]

tert-Butyl N-[(1S,10S)-10-(6-amino-3-fluoropyridin-2-yl)-10-(fluoromethyl)-1-oxo-1λ⁶-thia-2,7,9-triazabicyclo[5.4.0]undeca-1,8-dien-8-yl]carbamate A11c (61 mg, 137 µmol) was coupled with 5-cyanopicolinic acid according to the Ghosez's reagent-method to give after flash chromatography (silica gel, 10 g, 0-80% EtOAc in heptane) the title compound (39 mg, 67.9 µmol, 49.5% yield) as a light yellow foam. MS (ESI): m/z=575.5 [M+H]⁺.

A12e (R³=CH₂F): tert-butyl N-[(1R,10S)-10-[6-[(5-cyanopyridine-2-carbonyl)amino]-3-fluoropyridin-2-yl]-10-(fluoromethyl)-1-oxo-1λ⁶-thia-2,7,9-triazabicyclo[5.4.0]undeca-1,8-dien-8-yl]carbamate

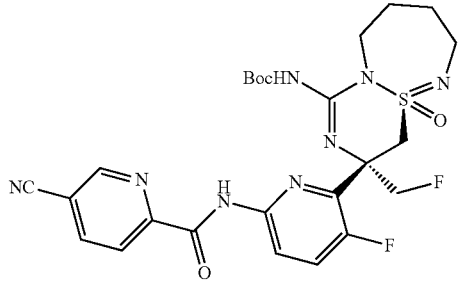 [SMILES: CC(C)(C)OC(=O)NC1=N[C@](CF)(c2nc(NC(=O)c3ccc(C#N)cn3)ccc2F)C[S@]2(=O)=NCCCCN12]

tert-Butyl N-[(1R,10S)-10-(6-amino-3-fluoropyridin-2-yl)-10-(fluoromethyl)-1-oxo-1λ⁶-thia-2,7,9-triazabicyclo[5.4.0]undeca-1,8-dien-8-yl]carbamate A11d (76 mg, 171 µmol) was coupled with 5-cyanopicolinic acid according to the Ghosez's reagent-method to give after flash chromatography (silica gel, 10 g, 0-80% EtOAc in heptane) the title compound (84 mg, 146 µmol, 85.5% yield) as a yellow foam. MS (ESI): m/z=575.5 [M+H]⁺.

Example 1

5-Cyano-pyridine-2-carboxylic acid [6-((3R,4aR)-1-amino-3-methyl-4a-oxo-3,4,6,7,8,9-hexahydro-4aλ⁶-thia-2,5,9a- triaza-benzocyclohepten-3-yl)-5-fluoro-pyridin-2-yl]-amide ((3R,4aR)-3-{6-[(5-Cyano-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester (60 mg, 64.7 µmol, Eq: 1.00) was deprotected with TFA in DCM to give after flash chromatography (SiO₂, 5 g, 0-10% MeOH in EtOAc) the title compound (12 mg, 26.3 µmol, 40.6% yield) as a light brown solid. MS (ISP): m/z=457.2 [(M+H)⁺].

Example 2

5-Cyano-pyridine-2-carboxylic acid [6-((3R,4aS)-1-amino-3-methyl-4a-oxo-3,4,6,7,8,9-hexahydro-4aλ⁶-thia-2,5,9a- triaza-benzocyclohepten-3-yl)-5-fluoro-pyridin-2-yl]-amide ((3R,4aS)-3-{6-[(5-Cyano-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester (144 mg, 186 µmol, Eq: 1.00) was deprotected with TFA in DCM to give after flash chromatography (SiO₂, 5 g, 0-10% MeOH in EtOAc+DCM/MeOH/NH₄OH 110:10:1) the title compound (53 mg, 116 µmol, 62.3% yield) as an off-white solid. MS (ISP): m/z=457.3 [(M+H)⁺].

Example 3

5-Cyano-3-methyl-pyridine-2-carboxylic acid [6-(3R,4aS)-1-amino-3-methyl-4a-oxo-3,4,6,7,8,9-hexahydro-4aλ⁶-thia-2,5,9a-triaza-benzocyclohepten-3-yl)-5-fluoro-pyridin-2-yl]-amide ((3R,4aS)-3-{6-[(5-Cyano-3-methyl-pyridine-2-carbonyl)-amino]-3-fluoro-pyridin-2-yl}-3-methyl-4a-oxo-3,4,6,7,8,9-hexahydro-4aλ⁶-thia-2,5,9a-triaza-benzocyclohepten-1-yl)-carbamic acid tert-butyl ester (70 mg, 85.9 µmol, Eq: 1.00) was deprotected with TFA in DCM to give after flash chromatography (SiO₂, 10 g, 0-10% MeOH in EtOAc+

DCM/MeOH/NH$_4$OH 110:10:1) the title compound (18 mg, 38.3 µmol, 44.6% yield) as a light brown foam. MS (ISP): m/z=471.3 [(M+H)$^+$].

Example 4

N-[6-[(1S,10S)-8-Amino-10-(fluoromethyl)-1-oxo-1λ$^6$-thia-2,7,9-triazabicyclo[5.4.0]undeca-1,8-dien-10-yl]-5-fluoropyridin-2-yl]-5-cyanopyridine-2-carboxamide tert-Butyl N-[(1S,10S)-10-[6-[(5-cyanopyridine-2-carbonyl)amino]-3-fluoropyridin-2-yl]-10-(fluoromethyl)-1-oxo-1λ$^6$-thia-2,7,9-triazabicyclo[5.4.0]undeca-1,8-dien-8-yl]carbamate (39 mg, 67.9 µmol, Eq: 1.00) was deprotected with TFA in DCM to give after flash chromatography (SiO$_2$, 5 g, 0-10% MeOH in EtOAc+DCM/MeOH/NH$_4$OH 110:10:1) the title compound (8.5 mg, 17.9 µmol, 26.4% yield) as an off white solid. MS (ISP): m/z=475.2 [(M+H)$^+$].

Example 5

N-[6[(1R,10S)-8-Amino-10-(fluoromethyl)-1-oxo-1λ$^6$-thia-2,7,9-triazabicyclo[5.4.0]undeca-1,8-dien-10-yl]-5-fluoropyridin-2-yl]-5-cyanopyridine-2-carboxamide tert-Butyl N—[(R1R,10S)-10-[6-[(5-cyanopyridine-2-carbonyl)amino]-3-fluoropyridin-2-yl]-10-(fluoromethyl)-1-oxo-1λ$^6$-thia-2,7,9-triazabicyclo[5.4.0]undeca-1,8-dien-8-yl]carbamate (84 mg, 146 µmol, Eq: 1.00) was deprotected with TFA in DCM to give after flash chromatography (SiO$_2$, 5 g, 0-10% MeOH in EtOAc+DCM/MeOH/NH$_4$OH 110:10:1) the title compound (42 mg, 88.5 µmol, 60.5% yield) as a light yellow foam. MS (ISP): m/z=475.2 [(M+H)$^+$].

The invention claimed is:

1. A compound of formula Ia:

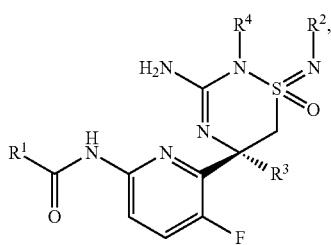

Ia or a pharmaceutically acceptable salt thereof, wherein:

R$^1$ is selected from the group consisting of
  i) aryl,
  ii) aryl, substituted by 1 or 2 substituents individually selected from cyano, C$_{1-6}$-alkyl, halogen-C$_{1-6}$-alkyl and halogen,
  iii) heteroaryl, and
  iv) heteroaryl, substituted by 1 or 2 substituents individually selected from cyano, C$_{1-6}$-alkyl, halogen-C$_{1-6}$-alkyl and halogen;

R$^2$ and R$^4$ are independently selected from the group consisting of
  i) —(CH$_2$)$_x$—, wherein x=3 or 4; substituted by 1 or 2 halogen-C$_{1-6}$-alkyl, and
  ii) —(CH$_2$)—(CY$_2$)$_z$—(CH$_2$)—, wherein each individual Y=H or F and z=1 or 2; and R$^3$ is selected from the group consisting of
  i) C$_{1-6}$-alkyl, and
  ii) halogen-C$_{1-6}$-alkyl.

2. The compound according to claim 1, wherein R$^1$ is heteroaryl, substituted by 1-2 substituents individually selected from cyano and C$_{1-6}$-alkyl.

3. The compound according to claim 1, wherein R$^1$ is pyridyl, substituted by 1-2 substituents individually selected from cyano and C$_{1-6}$-alkyl.

4. The compound according to claim 1, wherein R$^1$ is 5-cyano-3-methyl-pyridin-2yl or 5-cyano-pyridin-2yl.

5. The compound according to claim 1, wherein R$^2$ and R$^4$ together are —(CH$_2$)—(CY$_2$)$_z$—(CH$_2$)—, Y is H and z is 2.

6. The compound according to claim 1, wherein R$^3$ is C$_{1-6}$-alkyl.

7. The compound according to claim 1, wherein R$^3$ is methyl.

8. The compound according to claim 1, wherein R$^3$ is halogen-C$_{1-6}$-alkyl.

9. The compound according to claim 1, wherein R$^3$ is —CH$_2$F.

10. The compound according to claim 1, wherein R$^3$ is —CHF$_2$.

11. A pharmaceutical composition, comprising a compound according to claim 1, or a pharmaceutically acceptable salt thereof, and a pharmaceutically acceptable carrier and/or a pharmaceutically acceptable auxiliary substance.

12. A method of treating Alzheimer's disease, comprising the step of administering a therapeutically effective amount of a compound according to claim 1, or a pharmaceutically acceptable salt thereof, to a human being or animal in need thereof.

* * * * *